US006556866B2

United States Patent
Dal Molin et al.

(12) United States Patent
(10) Patent No.: US 6,556,866 B2
(45) Date of Patent: Apr. 29, 2003

(54) ACTIVE IMPLANTABLE MEDICAL DEVICE, IN PARTICULAR A PACEMAKER, DEFIBRILLATOR AND/OR CARDIOVERTOR OF THE MULTISITE TYPE PROVIDING RESYNCHRONIZATION OF THE VENTRICLES

(75) Inventors: Renzo Dal Molin, Chatillon (FR); Alain Ripart, Gif sur Yvette (FR)

(73) Assignee: Ela Medical S.A., Montrouge (FR)

( * ) Notice: Subject to any disclaimer, the term of this patent is extended or adjusted under 35 U.S.C. 154(b) by 226 days.

(21) Appl. No.: 09/739,614

(22) Filed: Dec. 18, 2000

(65) Prior Publication Data

US 2001/0012953 A1 Aug. 9, 2001

(30) Foreign Application Priority Data

Dec. 17, 1999 (FR) .............................. 99 16015

(51) Int. Cl.$^7$ ................................. A61N 1/365
(52) U.S. Cl. ............................. 607/9; 607/17
(58) Field of Search .................. 607/9, 15, 17, 607/18, 24, 27

(56) References Cited

U.S. PATENT DOCUMENTS 5,995,870 A   11/1999   Cazeau et al. ............... 607/9

FOREIGN PATENT DOCUMENTS

| EP | 0 862 927 A1 | 9/1998 | .......... A61N/1/365 |
| WO | 99/30777 | 12/1998 | .......... A61N/1/368 |

Primary Examiner—Jeffrey R. Jastrzab
(74) Attorney, Agent, or Firm—Orrick, Herrington & Sutcliffe LLP

(57) ABSTRACT

An active implantable medical device, in particular a pacemaker, defibrillator and/or cardiovertor of the multisite type providing resynchronization of the ventricles electrodes are placed in at least two sites, right and left, and are connected to a circuit for the collection of cardiac signals, to detect a depolarization potential. Electrodes also are connected to a stimulation circuit, to apply stimulation pulses to at least some of the sites. The device provides resynchronization of the ventricular contraction, by establishing a delay between the times of application of the respective stimulation pulses on the right ventricle (RV) and left ventricle (LV), determining a parameter (z) representative of the degree of synchronization between ventricles, and varying the delay in the direction of the improvement of the aforesaid representative parameter. The parameter is a bio-impedance measurement.

9 Claims, 1 Drawing Sheet

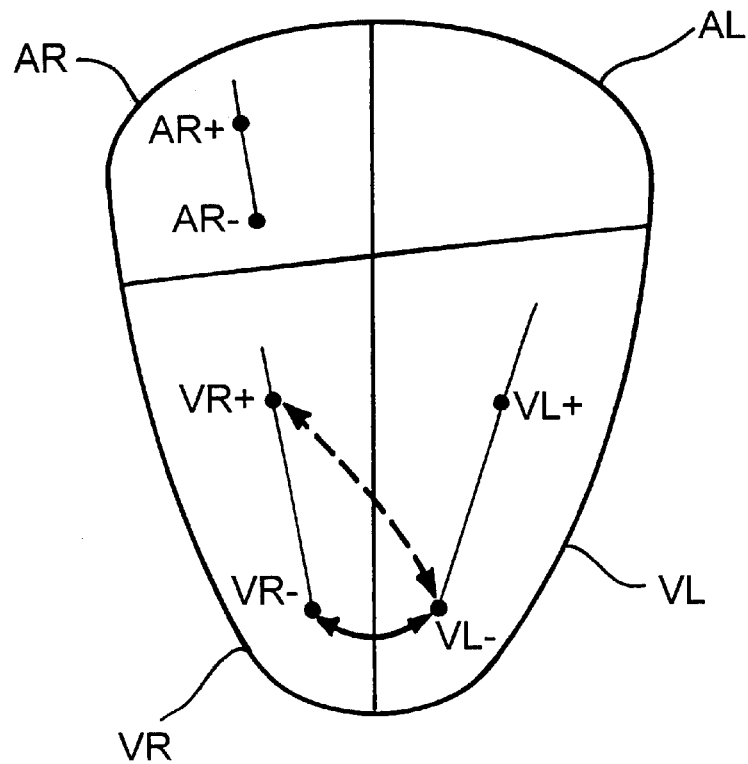
FIG_1
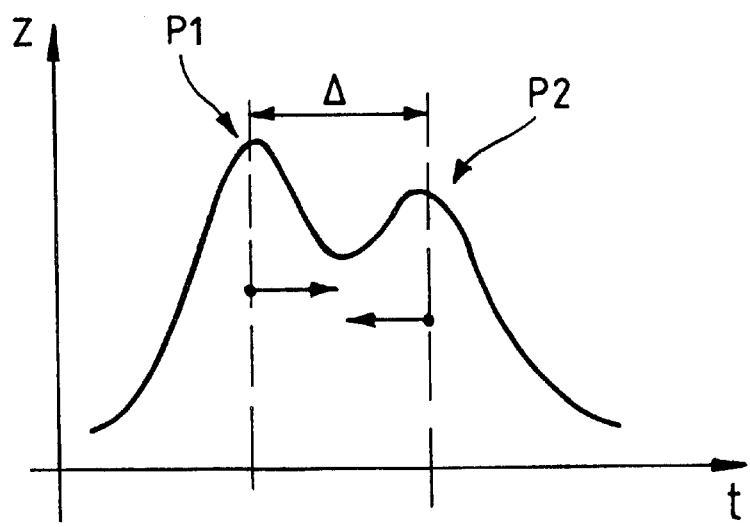
FIG_2

ACTIVE IMPLANTABLE MEDICAL DEVICE, IN PARTICULAR A PACEMAKER, DEFIBRILLATOR AND/OR CARDIOVERTOR OF THE MULTISITE TYPE PROVIDING RESYNCHRONIZATION OF THE VENTRICLES

FIELD OF THE INVENTION

The present invention relates to "active implantable medical devices" as such devices are defined by the Jun. 20, 1990 directive 90/385/CEE of the Council of the European Communities, more particularly to pacemaker, defibrillator and/or cardiovertor devices which are able to deliver to the heart low energy stimulation pulses for the treatment of the cardiac rate disorders, and even more particularly to the so-called "multisite" prostheses in which electrodes are placed in a plurality of distinct respective cardiac sites, comprising at least one ventricular site and one atrial site.

BACKGROUND OF THE INVENTION

Multisite prosthesis are known and include the following types: "double chamber" (right atrial stimulation and right ventricular stimulation), "triple chamber" (right atrial stimulation and double ventricular stimulation), and "quadruple chamber" (double atrial stimulation and double ventricular stimulation).

In addition to the treatment of cardiac disorders, it has been proposed to treat by stimulation myocardial contraction disorders which are observed among patients having a cardiac insufficiency. These disorders may be spontaneous or induced by a traditional stimulation pulse. One will be able, in particular, to refer to the study of J. C. Daubert et al., Stimucoeur, 25, n°3, pp. 170–176, which gives a report on work with respect to this subject.

Daubert et al. proposed to stimulate simultaneously and permanently the left and right ventricles, for the resynchronization of both ventricles. One often can observe spectacular results by such treatment for patients having a Class-III type cardiac insufficiency, whose condition was not improved by the traditional treatments.

In practice, multisite devices preferably operate in synchronous stimulation. This means that the two ventricular stimulation sites receive stimulation pulses at the same time, i.e., there is no inter-ventricular delay. This is also called a bi-ventricular stimulation.

The starting point of the present invention lies in the observation by the inventors that this bi-ventricular stimulation with no inter-ventricular delay is not necessarily optimal, and, further, does not necessarily lead to a synchronous contraction of the two ventricles. Indeed, the times of conduction within the myocardium are not the same on the right and on the left sides, and the variance can depend on multiple factors, such as the site of the left ventricular probe, according to whether this probe is placed in the coronary sinus or an epicardial probe.

SUMMARY OF THE INVENTION

It is therefore, an object of the present invention to propose a device that is able to establish an inter-ventricular delay between two ventricular stimulations, and to adjust this delay so as to resynchronize the contraction of the ventricles, and thus to lead to a fine optimization of the patient's hémodynamic condition.

Broadly, the present invention is directed to a device which is, in a way in itself known, a device of the multisite type, for use with electrodes that are placed in at least two cardiac sites, right and left. These electrodes are connected to a circuit in the device for the collection (i.e., the sensing or detection) of cardiac signals, more specifically to detect a depolarization potential, as well as to a circuit in the device for the stimulation of the heart, more specifically to apply stimulation pulses to at least certain of the aforesaid sites.

According to the invention, the device also comprises means for resynchronization of the ventricular contractions, with means for establishing an inter-ventricular delay between the time of application of the respective stimulation pulses on the right and left ventricles, means for determining a parameter representative of the degree of synchronization between the ventricles and analyzing this parameter, and means for varying the inter-ventricular delay in the direction of the improvement of the aforesaid representative parameter.

According to an advantageous subsidiary characteristic of the invention, the means for determining the representative parameter comprise a hemodynamic sensor, in particular a sensor of an intracardiac bio-impedance measured dynamically between a right site and a left site, more preferably between a right ventricular site and a left ventricular site, or between a right atrial site and a left ventricular site. The measurement of impedance is preferably operated by injection of a current pulse between the right and left sites, and the collection of a differential potential between a right site and a left site, or between two right sites, or between two left sites.

The configuration of the bio-impedance measurement can be a quadripolar configuration, without a site common to the injection and the collection, or a tripolar configuration, with one site common to the injection and the collection. One particular a configuration is where the site common to the injection and the collection is a left ventricular distal site, the other injection site is a distal right ventricular site, and the other collection site is a right ventricular proximal site.

BRIEF DESCRIPTION OF THE DRAWINGS

Further features, characteristics, and advantages of the present invention will appear to a person of ordinary skill in the art in view of the following description of a preferred embodiment of the invention, made with reference to the drawings annexed, in which:

FIG. 1 is a schematic view of a cardiac muscle, with a plurality of various stimulation sites; and FIG. 2 is a representative illustration of the intracardiac variation of the bio-impedance over time, throughout a cardiac cycle.

DETAILED DESCRIPTION OF THE INVENTION

FIG. 1 represents schematically a cardiac muscle, with its four cavities: right atrium RA, left atrium LA, right ventricle RV and left ventricle LV.

To obtain a bi-ventricular stimulation, probes are typically placed in appropriate locations for the stimulation of each ventricle. For example, as illustrated, bipolar probes comprising a right ventricular proximal electrode RV+, a right ventricular distal electrode RV−, a left ventricular proximal electrode LV+ and a left ventricular distal electrode LV−.

A probe also can be implanted for the stimulation of the right atrium as illustrated, for example, a right proximal atrial electrode RA+ and a right distal atrial electrode RA−.

If necessary, it can be also envisaged to provide a probe on the left atrium, if one desires to carry out a collection of signals and/or a stimulation on the two atriums (quadruple chamber configuration).

The electrodes of the probes are thus connected to a case of a device including various signal collection (detection) circuits, stimulation circuits and control circuits for example, the case of multisite pacemaker such as that described in the EP-A-0 925 806 and the commonly owned and co-pending, corresponding U.S. application Ser. No. 09/218,678, filed Dec. 22, 1998, the disclosure of which is incorporated by reference herein in its entity, and to which one will refer for further details.

The introduction of an inter-ventricular delay of the stimulation and the adjustment of the delay, in accordance with the present invention, can be obtained by a suitable programming of a microprocessor for such microprocessor controlled devices to start the various stimulations at the selected times, or by a wired logic circuit structure configured to set adjustably the time of delivery of the respective stimulation pulses, or a combination of such hardware and software controls. The ability to select the connections between the different leads and the collection circuits and the stimulation circuits provides a flexibility in design for obtaining a configuration useful for implementing the present invention.

The inter-ventricular delay could be selected to be: (1) nul or none (0 ms); (2) positive, in that the the left ventricle is being stimulated after the right ventricle with a delay which can be as great as, for example, 48 ms; or (3) negative, in that the the right ventricle is stimulated after the left ventricle with a delay which can be as great as, for example, 48 ms.

The device further comprises a sensor able to deliver to the microprocessor a measured parameter which is or can be used as an indicator of the degree of synchronization of the contractions of the right and left ventricles. Advantageously, in a preferred embodiment, the sensor is a hemodynamic sensor which operates to measure a bio-impedance of a patient's cardiac activity. One such circuit for measuring bio-impedance which could be used is described, for example, in the Chirife U.S. Pat. No. 5,154,171. This document describes a method of measuring diastolic and systolic volumes of a ventricle based on a dynamic measurement of bio-impedance, thus making it possible to obtain an indication of the cardiac flow and of the fraction of ejection, which is the hemodynamic parameter referenced in the Chirife patent.

The present invention proposes to use a circuit such as that described in the Chirife patent, but instead to adapt it to take an intracardiac bio-impedance measurement between a right site and a left site. The measurement of bio-impedance is classically done by injection of a pulse of current between two points, and collection of a differential potential between two points.

In the above mentioned Chirife U.S. Pat. No. 5,154,171, the points of injection and collection are the same (i.e., implementing a bipolar configuration), while in the present invention the preferred configurations of measurement are a tripolar configuration (one point common to the injection and the collection) or a quadripolar (no point common to the injection and the collection).

The injected current useful for the measurement of impedance, is for example, a current of 80 $\mu$A delivered in the form of a pulse of 5 $\mu$s width.

Various other configurations of circuits and pulses useful for the injection and collection of the bio-impedance measurement are possible, as will be appreciated by a person of ordinary skill in the art.

In a currently preferred embodiment, which implements a tripolar configuration, with reference to FIG. 1, the injection is made (as illustrated by the thick continuous arrows) between the right ventricular distal electrode RV− and the left ventricular distal electrode LV−, and the collection is made (as illustrated by the arrows in thick dashed lines) between the right ventricular proximal electrode RV+ and left ventricular distal electrode LV−.

All other tripolar or quadripolar configurations are foreseeable by combining two pairs of the six illustrated sites RV+, RV−, LV+, LV−, RA+ and RA−, the only excluded combinations being the combinations leading to a bipolar configuration, or where the injection of current is done on the same side of the heart. As noted, the injection should be realized between a right site and a left site.

The tripolar configurations currently preferred are:

injection between RV− and LV−, collection between RV+ and LV−, injection between RA− and LV−, collection between RA+ and LV−, and injection between RA− and LA−, collection between RA+ and RA−.

The injection and the collection of the signals in these various points are carried out by a circuit as described in the Chirife U.S. Pat. No. 5,154,171 above mentioned, or by a circuit such as that used for a measurement of the minute-ventilation (MV), which circuits already exist on known rate responsive cardiac stimulation devices. Such known rate response devices include the TALENT, CHORUM, and CHORUS RM model pacemakers available from ELA Medical, S.A. Montrouge France.

When used, the MV detection circuit is implemented in a modified manner in several respects. First, the sites are modified for intracardiac injection/collection, rather than the injection/detection transpulmonary between heart and case used for MV. Second, the collection is operated at a different frequency band than the frequency normally used for the measurement of MV. Preferably, a relatively higher frequency is used for the injection and collection for the inter-ventricular resynchronization according to the present invention. For example, a repetition rate of the injection of between 8 and 31 ms. is suitable.

Thus, the material part of the impedance measurement modules could be identical to what already exists in known pacemaker devices, thus allowing a realization of the invention without a large additional cost or design. This is a particularly advantageous result in that there is a lower cost of manufacture and development and a lesser time to bring the invention to market.

It should be understood that the measurement of the minute-ventilation also can be done by a current injection between right ventricular distal electrode RV− and the case of pacemaker, and the collection between the right ventricular proximal electrode RV+ and the case, thus permitting both measurements to be made using the same circuit structure, for added efficiency and economy.

The dynamic curve of the bio-impedance Z measured over time for one cardiac cycle is illustrated in a representative manner in FIG. 2. If the contraction of the ventricles are not synchronous, one observes two peaks of impedance P1 and P2 corresponding to the respective systoles of the two ventricles. The variation ($\Delta$) between these two peaks is representative of the degree of the interventricular desynchronization.

The device is then able to modify the timing of the delay of application of the stimulation pulses to the ventricles in the direction appropriate to improve the synchronism, i.e., in the direction of bringing together the two peaks P1 and P2. Ideally, peaks P1 and P2 are detected as a single peak when the ventricles contract in synchronism.

One skilled in the art will appreciate that the present invention can be implemented by embodiments other that the particular embodiments disclosed, which are presented for purposes of illustration, and not of limitation.

We claim:

1. An active implantable medical device of the multisite type to be connected to electrodes placed in at least one left cardiac site and at least one right cardiac site, said device having a cardiac signal collection circuit for connection to at least one of said electrodes to detect a depolarization potential, and a stimulation circuit to apply stimulation pulses to at least two of said sites through corresponding electrodes, said device comprising means for resynchronization of ventricular contractions, including:

(a) means for establishing a delay between a time of application of a stimulation pulse to a right ventricle (RV) and a stimulation pulse to a left ventricle (LV);

(b) means for determining and analyzing a parameter of a degree of desynchronization between contraction of said left and right ventricles for a cardiac cycle, said parameter indicating a variation between left and right ventricular systole; and (c) means for varying the delay in a direction of a reduction of the parameter of the degree of desynchronization.

2. The device of claim 1, wherein the means for determining the representative parameter further comprises a hemodynamic sensor.

3. The device of claim 2, wherein the hemodynamic sensor is a sensor of a dynamic intracardiac bio-impedance between a left side and a right side.

4. The device of claim 3, wherein the hemodynamic sensor is a sensor of a dynamic intracardiac bio-impedance between a right ventricular site (RV+, RA−) and a left ventricular site (LV+, LV−).

5. The device of claim 3, wherein the hemodynamic sensor is a sensor of dynamic intracardiac bio-impedance (z) between a right atrial site (RA+, RA−) and a left ventricular site (LV+, LV−).

6. The device of claim 3, wherein the means for determining said parameter further comprises means for injecting a current between a right site and a left site, and collecting a differential potential between two sites selected from among the group consisting of a right site and a left site, two right sites, and two left sites.

7. The device of claim 6, wherein the hemodynamic sensor is configured for obtaining the bio-impedance measurement in a tripolar lead configuration, with one site common to the injection of current and the collection of the differential potential.

8. The device of claim 7, in which one site common to the injection and the collection is a left ventricular distal site (RV−), the other site of injection is a distal right ventricular site (LV−) and the other site of collection is a proximal right ventricular site (RV+).

9. The device of claim 6, wherein the hemodynamic sensor is configured for obtaining the measurement in a quadripolar lead configuration, without a site common to the injection and the collection.

* * * * *

UNITED STATES PATENT AND TRADEMARK OFFICE
CERTIFICATE OF CORRECTION

PATENT NO. : 6,556,866 B2
DATED : April 29, 2003
INVENTOR(S) : Renzo Dal Molin and Alain Ripart It is certified that error appears in the above-identified patent and that said Letters Patent is hereby corrected as shown below:

Column 2,
Line 35, after "particular" delete "a";

Column 3,
Line 10, delete "entity" and insert -- entirety -- therefor;
Lines 26 and 29, delete "the the" and insert -- the -- therefor;
Line 59, after "quadripolar" insert -- configuration --;

Column 5,
Line 6, delete "that" and insert -- than -- therefor ;
Lines 22 and 28, after "parameter" insert -- representative --.

Signed and Sealed this

Third Day of May, 2005

JON W. DUDAS
*Director of the United States Patent and Trademark Office*